United States Patent
Lee et al.

(10) Patent No.: US 9,433,699 B2
(45) Date of Patent: Sep. 6, 2016

(54) HYDROGEL COMPRISING CATECHOL GROUP-COUPLED CHITOSAN OR POLYAMINE AND POLOXAMER COMPRISING THIOL GROUP COUPLED TO END THEREOF, PREPARATION METHOD THEREOF, AND HEMOSTAT USING SAME

(75) Inventors: Haeshin Lee, Daejeon (KR); Moon Sue Lee, Seoul (KR); Ji Hyun Ryu, Daejeon (KR)

(73) Assignee: INNOTHERAPY INC., Seoul (KR)

( * ) Notice: Subject to any disclaimer, the term of this patent is extended or adjusted under 35 U.S.C. 154(b) by 112 days.

(21) Appl. No.: 14/239,538

(22) PCT Filed: Nov. 21, 2011

(86) PCT No.: PCT/KR2011/008880
§ 371 (c)(1),
(2), (4) Date: Mar. 6, 2014

(87) PCT Pub. No.: WO2013/077476
PCT Pub. Date: May 30, 2013

(65) Prior Publication Data
US 2014/0193360 A1    Jul. 10, 2014

(30) Foreign Application Priority Data
Nov. 21, 2011   (KR) ........................ 10-2011-0121482

(51) Int. Cl.
| | |
|---|---|
| *A61K 8/72* | (2006.01) |
| *A61L 24/08* | (2006.01) |
| *A61L 24/00* | (2006.01) |
| *A61L 24/04* | (2006.01) |
| *A61K 51/12* | (2006.01) |
| *A61K 9/06* | (2006.01) |

(52) U.S. Cl.
CPC ............ *A61L 24/08* (2013.01); *A61L 24/0015* (2013.01); *A61L 24/0031* (2013.01); *A61L 24/0042* (2013.01); *A61L 24/043* (2013.01); *A61K 9/06* (2013.01); *A61K 51/1213* (2013.01); *A61L 2400/04* (2013.01)

(58) Field of Classification Search
None
See application file for complete search history.

(56) References Cited

U.S. PATENT DOCUMENTS

| | | | |
|---|---|---|---|
| 5,496,872 | A | 3/1996 | Constancis et al. |
| 5,773,033 | A | 6/1998 | Cochrum et al. |
| 6,048,515 | A | 4/2000 | Kresse et al. |
| 6,200,595 | B1 | 3/2001 | Motoyashiki et al. |
| 6,310,188 | B1 | 10/2001 | Mukherjee |
| 6,329,337 | B1 | 12/2001 | Morita et al. |
| 6,991,652 | B2 | 1/2006 | Burg |
| 2009/0180966 | A1 | 7/2009 | Borbely et al. |
| 2011/0206771 | A1 | 8/2011 | Choi et al. |
| 2012/0225012 | A1 | 9/2012 | Asada et al. |

FOREIGN PATENT DOCUMENTS

| | | |
|---|---|---|
| JP | 2010-512230 A | 4/2010 |
| KR | 10-2008-0017161 A | 2/2008 |
| KR | 10-2010-0048751 A | 5/2010 |
| KR | 10-2011-0066615 A | 6/2011 |
| WO | 2008073938 A2 | 6/2008 |
| WO | 2011062227 A1 | 5/2011 |

OTHER PUBLICATIONS

Ryu, J., et al., "Catechol-Functionalized Chitosan/Pluronic Hydrogels for Tissue Adhesives and Hemostatic Materials", "Biomacromolecules", May 21, 2011, pp. 2653-2659, vol. 12, No. 7.

*Primary Examiner* — James Rogers
(74) *Attorney, Agent, or Firm* — Hultquist, PLLC; Steven J. Hultquist (57) ABSTRACT

The present invention relates to an adhesive hydrogel composition containing catechol group-coupled chitosan and Pluronic comprising a thiol group coupled to the end thereof, and more specifically, to an adhesive composition which is safe in vivo and in vitro, is temperature sensitive, and has an excellent hemostatic effect and thus can be used as a bioadhesive, and a medical adhesive, an adhesion barrier and a surface adsorption inhibitor comprising the same.

16 Claims, 4 Drawing Sheets

HYDROGEL COMPRISING CATECHOL GROUP-COUPLED CHITOSAN OR POLYAMINE AND POLOXAMER COMPRISING THIOL GROUP COUPLED TO END THEREOF, PREPARATION METHOD THEREOF, AND HEMOSTAT USING SAME

CROSS-REFERENCE TO RELATED APPLICATIONS

This application is a U.S. national phase under the provisions of 35 U.S.C. §371 of International Patent Application No. PCT/KR11/08880 filed Nov. 21, 2011, which in turn claims priority of Korean Patent Application No. 10-2011-00121482 filed Nov. 21, 2011. The disclosures of such international patent application and Korean priority patent application are hereby incorporated herein by reference in their respective entireties, for all purposes.

TECHNICAL FIELD

The present invention relates to an adhesive hydrogel composition, which comprises a catechol group-coupled chitosan and a Pluronic thiol group-coupled to the end thereof, and more particularly to an adhesive composition, which is stable in vivo and in vitro, is temperature-sensitive, has an excellent hemostatic effect, and thus can be used as a bioadhesive agent, and to an adhesive agent, an anti-adhesive agent and a surface adsorption-preventing agent for medical use, which comprise the adhesive composition.

BACKGROUND ART

An adhesive is a material that is used to bond an object to the surface of another object. According to the International Standards Organization (ISO), "adhesion" is defined as the state in which two surfaces are held together by chemical or physical forces or both, and "adhesive" is a material capable of holding at least two surfaces together. Adhesives are widely used in daily life and various industrial fields due to their convenience and are classified according to their main component into organic adhesives and inorganic adhesives. The organic adhesives are classified into synthetic organic adhesives and natural organic adhesives, and the synthetic organic adhesives are classified into resin-based adhesives including thermosetting resin or thermoplastic resin, rubber-based resins, and mixed adhesives including phenol and epoxy. However, the synthetic organic adhesives have the problem of emitting harmful substances. This problem is caused by the use of volatile organic solvents among organic solvents and volatilization of unreacted monomers. Particularly, in the case of adhesives for use in interior materials for buildings, regulations regarding the emission of harmful substances such as formaldehyde have been strengthened. Under these circumstances, glue-, soy bean protein- and tannin-based adhesives have been developed.

"Pressure sensitive adhesive" may appear as a kind of adhesives and refers to a material that adheres sufficiently to an adherend even by finger pressure, has a low cohesive force and shows a quick stress relaxation compared to an adhesive, and shows a viscoelastic behavior that can be readily deformed by external forces. Raw materials that are used in pressure sensitive adhesives are natural rubber, synthetic rubber, and thermoplastic resins such as acrylic resin and silicone resin, and mostly have elasticity. Unlike adhesives, pressure sensitive adhesives can maintain their adhesive forces even when being repeatedly used several times and have a property that they adhere stickily to adherends, which is called "stickiness".

Research and development in the field of tissue adhesives, including sealants and hemostats, is growing rapidly. Since a fibrin sealant was approved by the US FDA in the year 1998, new tissue adhesives have been developed annually. Such tissue adhesives are spotlighted as materials capable of substituting for technologies such as suturing, clipping or cautery, which are used in conventional surgical operations or medical procedures.

Conventional surgical techniques such as suturing have strong tensile strength, but suffer from problems such as patient's pain and post-surgical removal. Meanwhile, tissue adhesives have many advantages in that these adhere within a short time, are convenient to use and do not need to be removed after surgery, but have shortcomings in their adhesiveness and tensile strength are low and their adhesiveness significantly decreases in the presence of water. Studies have been conducted to overcome such shortcomings of tissue adhesives.

Tissue adhesives come in direct contact with tissue, and thus are required to be biocompatible. In addition, adhesives for medical use are generally used in vivo, and when they flow into body fluids and blood, they are involved in vivo, and for this reason, they should be free of toxicity and harmfulness under more strict conditions and should be biocompatible and biodegradable.

Generally, tissue adhesives are used in various areas, including skin, blood vessels, digestive system, brain nerve, plastic surgery, orthopedic surgery and the like, and thus they requires different properties, but mainly require the following characteristics: 1) they should adhere quickly at room temperature and atmospheric pressure even in the presence of water; 2) they should be non-toxic and should be able to be sterilized; 3) they should maintain sufficient mechanical strength in close contact with the wound surface; 4) they should be biodegradable and should be able to exhibit a hemostatic effect; and 5) they should be effective in the healing of the body.

Tissue adhesives that are currently commercialized or practically used include cyanoacrylate instant adhesives, fibrin glue, gelatin glue and polyurethane-based adhesives. The cyanoacrylate instant adhesives have recently received attention in studies on instant adhesives having high functionality and high performance. Particularly, medical instant adhesives for tissue suture having biocompatibility, flexibility and low toxicity have hemostatic and antibacterial effects and can substitute for suture materials, and thus have been actively studied mainly in advanced countries.

Such cyanoacrylate-based tissue adhesives are currently commercially available under trade names such as Dermabond (Johnson & Johnson) and Indermil (US Surgical). Such cyanoacrylate-based tissue adhesives have advantages in that they are composed of single materials, are hardened by water within a short time even in the absence of an initiator and have a transparent appearance and high adhesive strength, but have disadvantages of low impact resistance and heat resistance. In addition, these adhesives are not substantially used due to their high toxicity and are partially used in clinical applications in countries other than the USA, but the use thereof is limited due to the tissue toxicity and side effect thereof.

Moreover, the fibrin glue adhesive was approved in 1998 by the US FDA for use in cardiac surgery. Since then, studies on fibrin tissue adhesives have been actively conducted, and products such as Tisseel VH (Baxer) and Evicel™ (Johnson & Johnson) are currently commercially available.

The fibrin tissue adhesives together with the cyanoacrylate-based adhesives account for the tissue adhesive market.

The fibrin tissue adhesives are clinically used to suture peripheral nerves and microvascular blood vessels, based on the cross-linking of fibrin, include fibrinogen, thrombin, calcium chloride and enzyme inhibitors.

Such fibrin glue adhesives have advantages in that they adhere quickly to target tissue without being influenced by water, can form a clot in conjunction with platelets without restrictions and have excellent biocompatibility. However, these have shortcomings in that they have a low adhesive strength, are quickly biodegraded and have the risk of infection.

Moreover, the gelatin glues are tissue adhesives derived from biological tissue and include a cross-linking product of gelatin-resorsinol-formalin (GRF).

In addition, there are tissue adhesives made of gelatin-glutaraldehyde. Although these tissue adhesives provide high adhesiveness, formalin or glutaraldehyde undergo crosslinking reactions with proteins in vivo, giving rise to tissue toxicity.

Developed as flexible adhesives, polyurethane adhesives can maintain the closures in their natural state following solidification. These adhesives absorb water from tissue surfaces to stick themselves fast to the tissues. They react with water to be hardened within several minutes and the hardened adhesives biodegrade properly in addition to being flexible. However, aromatic diisocyanate, a material used in polyurethane adhesives, is toxic to the body.

Thus, the tissue adhesives developed so far still have disadvantages in terms of toxicity and weak adhesiveness. To overcome these problems, studies on 3,4-dihydroxyphenyl-L-alanine (DOPA) that is a sea mussel-derived protein have recently been conducted.

Dopa is a naturally occurring amino acid and derived from the foot protein existed in the foot of mussels. It is the amino acid obtained by hydroxylation of tyrosine by polyphenol oxidase. This amino acid forms a very strong hydrogen bond with hydrophilic surfaces and a strong coordinate covalent bond with metals or semi-metals. Being oxidized to dopa-quinone, dopa residues function to crosslink protein molecules.

Dopa-based tissue adhesives are commercially available, identified as Cell-Tak™ (BD Bioscience Clontech) and MAP™ (Swedish BioScience Lab.). However, these products require as many as 10,000 mussels to make 1 gram of the foot protein. Such a low extraction yield and high production cost restrict the use of the adhesive. In practice, the products are used mainly in cell or tissue culturing.

According to a search on the USPTO database, only 14 patents have been filed with an abstract or claims containing chitosan and adhesive. Most of these patents are for the paper industry. U.S. Pat. No. 5,773,033 disclosed fibrinogen/chitosan hemostatic agents, but not for use in tissue bonding. U.S. Pat. No. 6,329,337 entitled "Adhesive for Biological Tissue" disclosed a glue agent produced from a recombinant human plasma protein and bifunctional or multifunctional aldehydes. Chitosan was used in the agent to enhance the viscosity of the solution or as a crosslinking reagent with bifunctional or multifunctional aldehydes. U.S. Pat. No. 5,496,872 disclosed chitosan in a fairly exhaustive list of potential reagents, but relies on thiols, carboxylic acids and radicals to bond. U.S. Pat. No. 6,200,595 disclosed a combination of polycationic substrates, including chitosan, along with polyanionic substrates to be used as a potential medical adhesive. Reported bond strengths in this patent did not exceed 70 g-f/cm$^2$. Additionally, this invention requires mixing of two components immediately prior to use. U.S. Pat. No. 6,991,652 disclosed the use of chitosan as one in a list of many potential materials to be used as a matrix for cellular growth.

A survey of the literature revealed that dialysis of chitosan has been used as a purification step and as a means for introducing coadditives. For example, U.S. Pat. No. 6,310,188 utilizes dialysis of chitosan to remove low-molecular-weight compounds.

Although a number of systems have been considered for use in the area of tissue adhesives, the currently available systems suffer from deficiencies including toxicity, insufficient strength, or difficulty in use. Thus, there is a need in the art for additional compositions that are safe and effective tissue adhesives that can be provided in a sterile and easy-to-use form. Such highly adherent compositions would also offer significant advantages in drug delivery. There is also a need in the art for compositions that remain highly hydrated, offering novel fillers, bulking compositions, or reconstructive compositions for use in cosmetic and reconstructive surgical procedures.

DISCLOSURE OF INVENTION

Technical Problem

In order to solve the above-described problems occurring in the prior art, the present inventors have developed an adhesive hydrogel, which comprises a compound having a catechol group-coupled chitosan or polyamine harmless to the human body and a compound having a polaxamer thiol group-coupled to both ends of polaxamer and has excellent biocompatibility and mechanical strength, is temperature-sensitive and has excellent tissue adhesion, thereby completing the present invention.

It is, therefore, an object of the present invention to provide an adhesive hydrogel which comprises a compound having a catechol group-coupled chitosan or polyamine and a compound having a thiol group-coupled to both ends of polaxamer.

Another object of the present invention is to use an adhesive hydrogel, which comprises a compound having a catechol group-coupled chitosan or polyamine and a compound having a thiol group-coupled to both ends of polaxamer, as a medical bioadhesive agent, an anti-adhesive agent and a surface adsorption-preventing agent.

Still another object of the present invention is to provide a method for preparing an adhesive hydrogel which comprises a compound having a catechol group-coupled chitosan or polyamine and a compound having a thiol group-coupled to both ends of polaxamer.

Technical Solution

To achieve the above objects, the present invention provides an adhesive hydrogel composition comprising: (i) a catechol group-coupled chitosan or polyamine; and (ii) a polaxamer thiol group-coupled to the end thereof.

Chitosan is a cationic polysaccharide derived by partially deacetylating chitin from the exoskeletons of shells, including shrimps, lobsters and crabs. The chemical properties of chitosan are well described as the deacetylated (1,4)-N-acetyl-D-glucosamine polymer. The adhesive property of chitosan is known for some cases. However, an adhesive product based on chitosan has not yet been produced. This is because chitosan is difficult to handle due to its solubility in concentrated acidic solutions and is difficult to deliver so as to adhere quickly to tissue.

The catechol group that is described in the present invention is represented by the following formula 1:

Formula 1

The catechol group-coupled chitosan or polyamine preferably has a molecular weight of 10,000 Da~1,000,000 Da, and more preferably 50,000 Da~200,000 Da, in view of the stability and adhesive strength of the hydrogel.

Specifically, the catechol group-coupled polyamine is preferably any one or more selected from the group consisting of ethylene diamine, 1,3-diaminopropane, hexamethylenediamine, tetraethylmethylenediamine, putrescine, cadaverine, spermidine, spermine, linear polyethyleneimine, branched polyethyleneimine, ε-poly-L-lysine, and poly(allylamine hydrochloride), and more preferably any one or more selected from the group consisting of linear polyethyleneimine, branched polyethyleneimine, ε-poly-L-lysine, and poly(allylamine hydrochloride), but is not limited thereto.

Polaxamer is a temperature-sensitive polymer that is liquid at low temperatures and solid at the body temperature and is suitably used as an injectable material.

The polaxamer that is described in the present invention is a hydrogel composition that is Pluronic represented by the following formula 2 or Tetronic represented by the following formula 3. The Pluronic is a block copolymer having a structure of polyethylene oxide (PEO)-polypropylene oxide (PPO)-polyethylene oxide (PEO), and specific examples thereof include, but are not limited to, F38, F68, F77, F77, F98, F108 and F127 derivatives, L31, L42, L43, L44, L62, L72 and L101 derivatives, and P75, P103 and P104 derivatives. The Tetronic is a block copolymer having four polypropylene oxide (PPO)-polyethylene oxide (PEO) functionalities in the ethylenediamine end, and specific examples thereof include, but are not limited, 1107, 1307, 130r2, 150r1, 304, 701, 702, 704, 901, 904, 908, and 90r4.

Formula 2 wherein a is an integer ranging from 2 to 200; and b is an integer ranging from 10 to 100; Preferably, a is an integer ranging from 2 to 141; b is an integer ranging from 16 to 69; and the ratio of a:b is ranging from 1:9 to 8:2.

Formula 3 wherein a is an integer ranging from 2 to 600; and b is an integer ranging from 10 to 150; Preferably, a is an integer ranging from 10 to 455; b is an integer ranging from 17 to 116; and the ratio of a:b is ranging from 1:9 to 9:1.

The Pluronic having a thiol group-coupled to the end or the Tetronic having a thiol group-coupled to the end most preferably have a molecular weight of 500 Da~500,000 Da in view of close packing after micelle formation and stable chemical coupling with chitosan having a catechol group coupled thereto.

According to the present invention, a catechol group is coupled to chitosan or polyamine, and a thiol group is coupled to both end of polaxamer, whereby the adhesive hydrogel of the present invention is excellent in terms of temperature sensitivity, an elastic modulus of at least 1 kPa, in vivo stability and quick and strong adhesion, compared to conventional bioadhesive hydrogels.

In addition, the adhesive composition of the present invention comprises water, a lower alcohol or a mixture thereof. The lower alcohol refers to an alcohol having a small number of carbon atoms (1 to 6 carbon atoms) in the alcohol molecule. The lower alcohol is a neutral compound that dissolves in water, but is not ionized and generates no ion, and it does not show alkalinity because the OH group thereof differs in nature from the OH group of a base. Examples of the lower alcohol include, but are not limited to, methanol, ethanol, n-propanol, isopropanol, butanol, amyl alcohol, n-amyl alcohol, isoamyl alcohol, n-hexyl alcohol and the like. The lower alcohol that is used in the adhesive composition of the present invention may preferably be ethanol.

In addition, the adhesive composition of the present invention may comprise additives for improving the physical properties of the composition, and the additives can be suitably selected by those skilled in the art.

The term "adhesion" in a general sense means that it is solidified at an initial stage with the passage of time to lose elasticity and is difficult to adhere again after detachment. However, as used herein, the term "adhesion" is meant to include "pressure sensitive adhesion", and the term "pressure sensitive adhesion" means that a pressure sensitive adhesive can easily adhere to an adherend by pressure while maintaining its viscoelastic property and can adhere to the adherend again several times after detachment. The adhesive composition of the present invention has a pressure sensitive adhesive property.

The adhesive composition of the present invention comprises, based on the total weight of the composition, 0.1-wt % of catechol group-coupled chitosan, 3-50 wt % of Pluronic having a thiol group-coupled to the end thereof, and 35-90 wt % of water, a lower alcohol or a mixture thereof, but is not limited thereto. More preferably, the adhesive composition of the present invention may comprise 0.5-10 wt % of catechol group-coupled chitosan, 8-20 wt % of Pluronic having a thiol group-coupled to the end thereof, and 75-90 wt % of water, a lower alcohol or a mixture thereof. Most preferably, it may comprise 0.5-4 wt % of catechol group-coupled chitosan, 10-18 wt % of Pluronic having a thiol group-coupled to the end thereof, and 80-85 wt % of water, a lower alcohol or a mixture thereof, in view of the stability and adhesive strength of the adhesive and easy injection during use.

The hydrogel composition of the present invention may further comprise a therapeutic drug.

Examples of the therapeutic drug that may be included in the hydrogel composition include poorly soluble drugs, therapeutic peptides, proteins or antibodies. Specifically, the therapeutic drug may include human growth hormones, erythropoietin, interferon, insulin, interleukin, calcitonin, G-CSF, angiopoietin, VEGF-Trap, monoclonal antibodies, antibody fragments, hemostatic proteins, antibiotics, analgesics, angina therapeutic agents to be administered sublingually, allergen extracts for sublingual immunotherapy of asthma and allergic nasitis, anti-histamines and anti-allergic agents.

The present invention relates to a medical adhesive comprising the adhesive composition.

The term "medical adhesive" in a broad sense refers to an adhesive that can be used in a wide range of applications, including the package of medical supplies, surgical sticking, adhesion and hemostasis, can be applied directly to the skin due to its biocompatibility, and has no toxicity and harmfulness in vivo even when being involved in vivo. The medical adhesive should have, in addition to biocompatibility, biodegradability, water resistance, sterilization ability, non-toxicity, and hemostatic effects, and should not interfere with healing of the body. The adhesive of the present invention may be used as medical adhesives, including pressure sensitive adhesives. More specifically, the adhesive of the present invention may be used in vivo as an adhesive hemostatic agent for surgical operations, and a medical adhesive for suture after large bowel resection.

The present invention also relates to an anti-adhesive agent comprising the adhesive composition.

As used herein, the term "anti-adhesive agent" refers to a substance that remains as a physical barrier in vivo for a specific period of time and acts to prevent adhesion between adjacent tissues. Thus, the anti-adhesive agent should be degraded or absorbed in vivo so that it does not remain as foreign matter. The adhesive composition of the present invention may be added in the preparation of an anti-adhesive agent that prevents adhesion from occurring after surgical operations.

The present invention also relates to a surface adsorption-preventing agent comprising the adhesive composition.

The present invention also provides a method for preparing a hydrogel, the method comprising:

(A) preparing a catechol group-coupled chitosan or polyamine;
(B) preparing a polaxamer thiol group-coupled to the end thereof;
(C) preparing a catechol-chitosan or catechol-polyamine solution by dissolving the catechol group-coupled chitosan or polyamine in a buffer;
(D) preparing a thiol-polaxamer solution by dissolving the polaxamer thiol group-coupled in a buffer;
(E) preparing an adhesive hydrogel solution by mixing the catechol-chitosan or catechol-polyamine solution of step (C) with the thiol-polaxamer solution of step (D); and
(F) gelatig the adhesive hydrogel solution of step (E).

Hereinafter, each step of the preparation method of the present invention will be described.

step (A) of preparing the catechol group-coupled chitosan or polyamine comprises the steps of:

(a) preparing a chitosan or polyamine solution by adding 0.2-5 parts by weight of chitosan or polyamine to 100 parts by weight of distilled water;
(b) preparing a hydrocaffeic acid solution by adding 1-5 parts by weight of hydrocaffeic acid and 2-10 parts by weight of 1-ethyl-3-(3-dimethylaminopropyl)-carbodiimide hydrochloride (EDC) to 100 parts by weight of distilled water;
(c) preparing a catechol group-coupled chitosan or polyamine mixture by mixing the chitosan or polyamine solution of step (a) with the hydrocaffeic acid solution of step (b) at a volume ratio of 1:1 to 3:1 and stirring the mixture; and
(d) purifying the catechol group-coupled chitosan or polyamine by dialyzing the catechol group-coupled chitosan or polyamine mixture of step (c) through a dialysis membrane in a buffer for 6-48 hours, and then drying purified catechol group-coupled chitosan or polyamine.

The buffer that is used in step (d) preferably has a pH of 4.5 to 5.5. If the pH is as low as less than 4.5, the content of hydrochloric acid in the final product can increase, and if the pH is as high as more than 5.5, the oxidation reaction of catechol can occur.

The dialysis in the buffer in step (d) is preferably carried out for 24-36 hours.

The catechol-coupled chitosan or polyamine preferably has a molecular weight of 10,000 Da~1,000,000 Da, and more preferably 50,000 Da~200,000 Da, in view of the stability and adhesive strength of the hydrogel.

The catechol group-coupled polyamine is one or more selected from the group consisting of ethylene diamine, 1,3-diaminopropane, hexamethylenediamine, tetraethylmethylenediamine, putrescine, cadaverine, spermidine, spermine, linear polyethyleneimine, branched polyethyleneimine, ε-poly-L-lysine, and poly(allylamine hydrochloride), and more preferably any one or more selected from the group consisting of linear polyethyleneimine, branched polyethyleneimine, ε-poly-L-lysine, and poly(allylamine hydrochloride), but is not limited thereto.

Step (A) is preferably carried out at a pH of 5 to 5.5. If the pH in step (A) is too low, the solubility of chitosan will increase, but hydrolysis of 1-ethyl-3-(3-dimethylaminopropyl)-carboimide hydrochloride will be accelerated, resulting in a reduction in conversion or yield, and if the pH is too high, the solubility of chitosan will decrease and thus precipitate will be formed, and hydrolysis of 1-ethyl-3-(3-dimethylaminopropyl)-carboimide hydrochloride will be accelerated, resulting in a reduction in conversion or yield.

Step (B) of preparing the polaxamer thiol group-coupled to the end thereof comprises the steps of:

(1) preparing a polaxamer solution by adding 5-15 parts by weight of polaxamer to 100 parts by weight of a non-polar organic solvent and 0.1-1 part by volume of triethylamine to 100 parts by volume of the non-polar organic solvent;

(2) preparing a nitrophenyl chloroformate solution by adding 5-20 parts by weight of nitrophenyl chloroformate to 100 parts by weight of a non-polar organic solvent;

(3) preparing a polaxamer mixture solution by mixing the polaxamer solution of step (1) with the nitrophenyl chloroformate solution of step (2) at a volume ratio of 5:1 to 10:1, and stirring the mixture;

(4) preparing a polaxamer mixture by precipitating and drying the polaxamer mixture solution of step (3);

(5) preparing a thiol group-coupled polaxamer mixture by adding 5-20 parts by weight of the polaxamer mixture of step (4) and 0.2-5 parts by weight of cysteamine to 100 parts by weight of a mixture of a non-polar organic solvent and a polar solvent, and stirring the mixture;

(6) preparing a thiol group-coupled Pluronic mixture by precipitating and drying the thiol group-coupled polaxamer mixture of step (5); and (7) purifying the thiol group-coupled Pluronic by dialyzing the thiol group-coupled Pluronic mixture of step (6) through a dialysis membrane in distilled water for 12-120 hours, and then drying purified thiol group-coupled Pluronic.

The Pluronic having the thiol group-coupled to the end or the Tetronic having the thiol group-coupled to the end most preferably has a molecular weight of 0.5 kDa~500 kDa in view of close packing after micelle formation and stable chemical coupling with the catechol group-coupled chitosan.

The catechol-chitosan or catechol-polyamine solution in step (C) is prepared by adding 0.1-10 wt % of the catechol group-coupled chitosan or polyamine to 100 wt % of the buffer, and the thiol-polaxamer solution in step (D) is prepared by 3-50 wt % of the thiol group-coupled polaxamer to 100 wt % of the buffer.

The adhesive hydrogel solution in step (E) is most preferably prepared by mixing the catechol-chitosan or catechol-polyamine solution with the thiol-polaxamer solution at a volume ratio of 1:3 to 3:1, in view of the convenience of use and the stability of the reaction. When the catechol-chitosan or catechol-polyamine solution is added to the thiol-polaxamer solution in an amount smaller than the lower limit of the above range described in the present invention, a high concentration of the catechol-chitosan or catechol-polyamine solution can be self-assembled at a pH of 6.5 or more to form a hydrogel without irritation, and the temperature sensitivity can decrease, and when the catechol-chitosan or catechol-polyamine solution is added to the thiol-polaxamer solution in an excessively large amount, it can be partially dissolved by a high concentration of the thiol-polaxamer solution, resulting in a decrease in the temperature sensitivity.

Step (F) of gelating the adhesive hydrogel solution is most preferably carried out at a temperature of 4 to 37° C. in view of the convenience of use and the use of the characteristics of a living body. If the gelating is carried out at a temperature lower than 4° C., a hydrogel can be formed even during cold storage so that it cannot be injected, and if it is carried out at a temperature higher than 37° C. that is higher than the living body temperature, the hydrogel solution will not be gelated in vivo and will be diffused.

Advantageous Effect

The hydrogel according to the present invention is stable in vivo and in vitro, is temperature-sensitive, has an excellent hemostatic effect, and thus can be used as a bioadhesive. In addition, it can be easily applied to an anti-adhesive agent and a surface adsorption preventing agent.

BEST MODE FOR CARRYING OUT THE INVENTION

Hereinafter, the present invention will be described in further detail with reference to examples. It is to be understood, however, that these examples are for illustrative purposes and are not intended to limit the scope of the present invention.

Preparation Example 1

Figure 1:
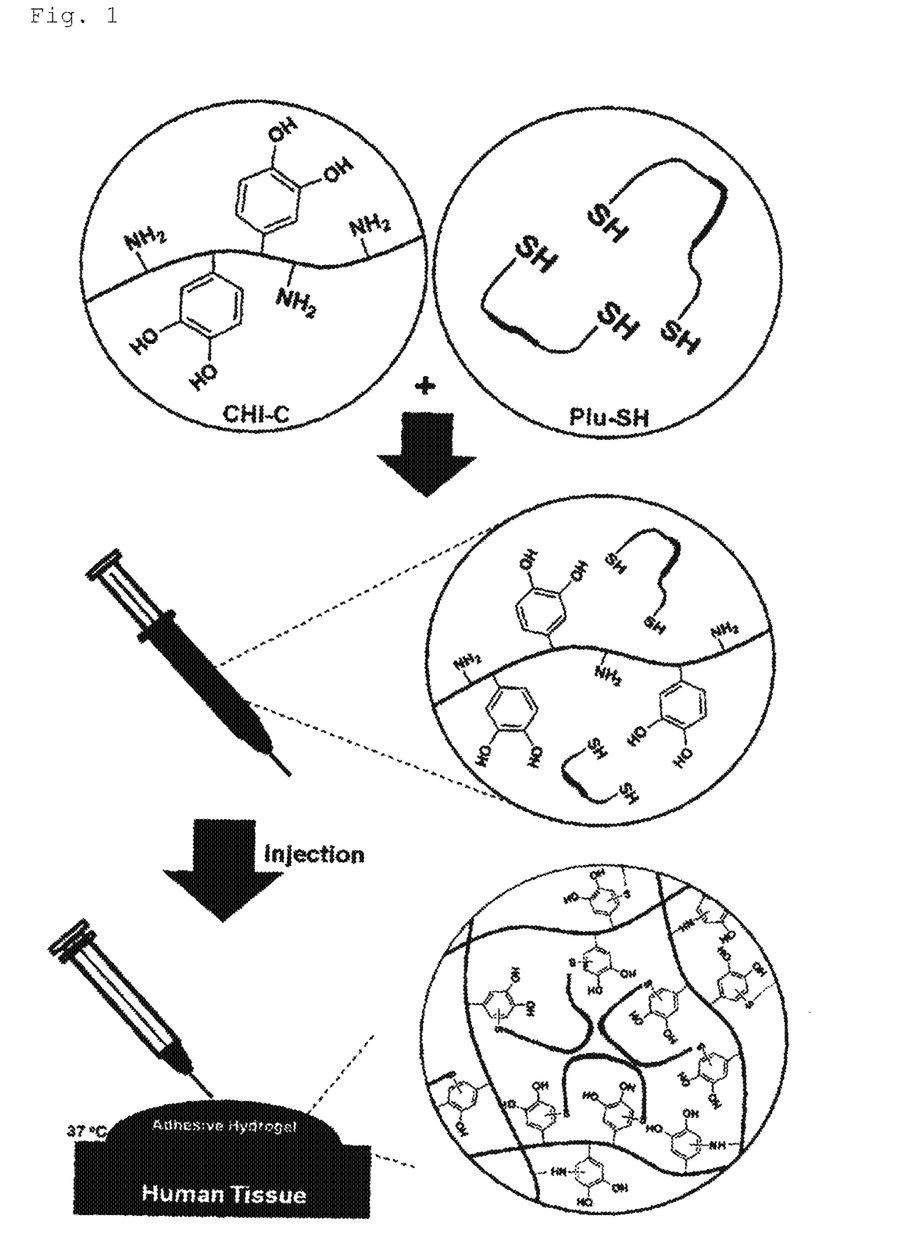
FIG. 1 is a schematic view of an adhesive hydrogel comprising a catechol group-coupled chitosan and a Pluronic having a thiol group-coupled to the end thereof, which has tissue adhesion, temperature sensitivity and gelling properties.
Figure 2:
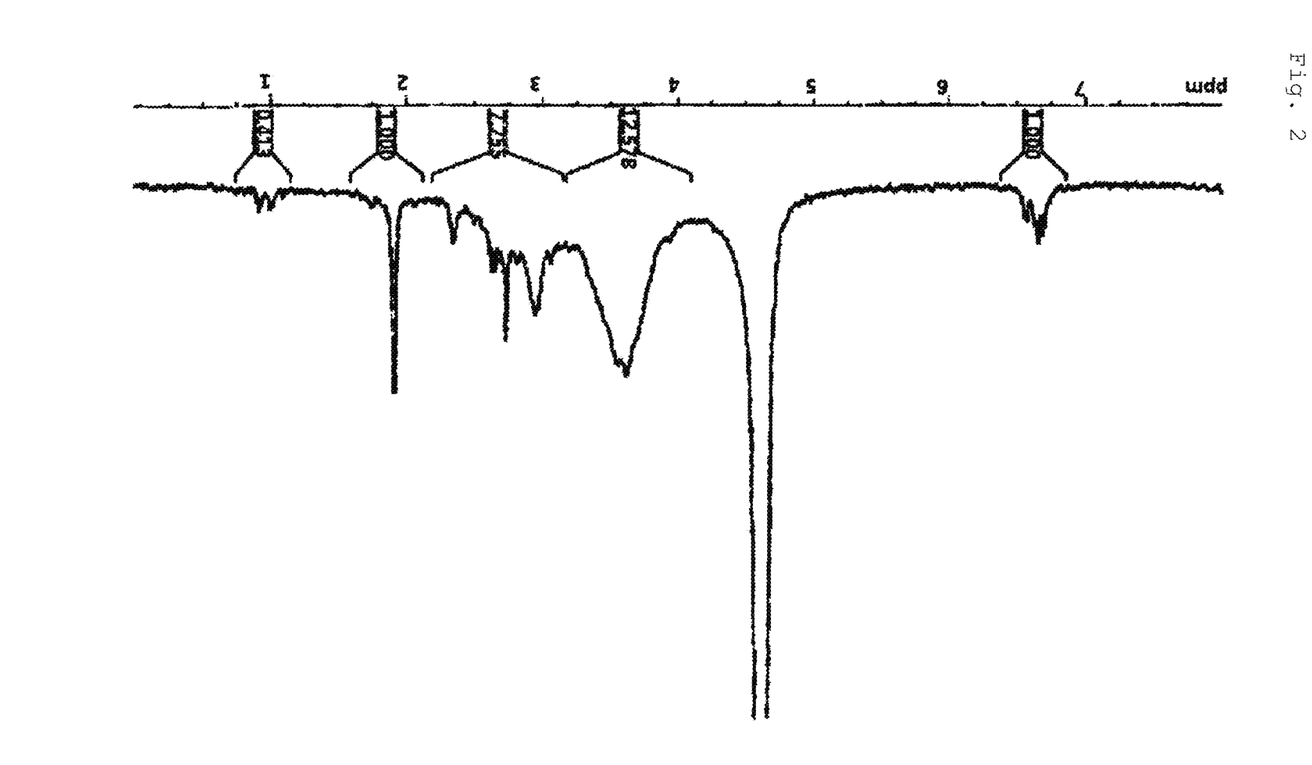
FIG. 2 is the nuclear magnetic resonance spectrum of a catechol group-coupled chitosan prepared in Preparation Example 1.

Preparation of Catechol Group-Coupled Chitosan 0.5 g of chitosan (Chitosan 300) was dissolved in 50 ml of 0.1M HCl solution to make a chitosan solution that could be maintained at a pH of 5 using 1M NaOH. 591.0 mg of hydrocaffeic acid (3,4-dihydroxy hydrocinnamic acid, Sigma-Aldrich) and 1244.9 mg of EDC (1-ethyl-3-(3-dimethylaminopropyl)-carbodiimide hydrochloride, Sigma-Aldrich) were dissolved in 25 ml of triple distilled water and added slowly to the chitosan solution. The mixture was allowed to react at room temperature for 12 hours while it maintained at a pH of 5.5 or less. The reaction product was dialyzed through a dialysis membrane (MWCO: 12,000-14,000, SpectraPor) at a pH of 5 for 2 days, and then dialyzed in triple distilled water for 4 hours. The dialyzed material was freeze-dried and then stored in a moisture-free desiccator. The content of catechol coupled to the chitosan was analyzed using nuclear magnetic resonance spectrometry and UV-Vis spectrometry. FIG. 2 shows a graph obtained by analyzing the catechol group-coupled chitosan by nuclear magnetic resonance spectrometry. It was shown that the content of catechol per chitosan molecule was 9.9%.

Preparation Example 2

Preparation of Polaxamer Having Thiol Group Coupled to End Thereof 10 g of Pluronic (Pluronic F-127) was dissolved in 70 ml of methylene chloride, and 221.2 μl of triethylamine was added thereto to prepare a Pluroinic solution. The prepared Pluronic solution was added slowly to 10 ml of a solution of 989.5 mg of p-nitrophenyl chloroformate in methylene chloride, and the mixture was stirred at room temperature for 24 hours, after which the volume of the solvent was reduced to 40 ml using an evaporator. The product was precipitated using dimethyl ether, and then dried under reduced pressure, thereby preparing activated Pluronic in the form of powder. 5 g of the activated Pluronic was dissolved in 20 ml of methylene chloride, and 423.4 mg of cysteamine was dissolved in 30 ml of a 1:1 (v/v) mixture of methylene chloride and ethanol, and the two solutions were mixed with each other and stirred at room temperature for 24 hours. After stirring, the product was precipitated using dimethyl ether, and then dried in reduced pressure to obtain powder. The obtained powder was dissolved in triple distilled water and dialyzed through a membrane (MWCO: 3,500, SpectraPor) for 96 hours, and the synthesized and purified material was freeze-dried, and then stored in a moisture-free desiccator. The content of the thiol group coupled to Pluroinic was measured using nuclear magnetic resonance spectrometry.

Figure 3:
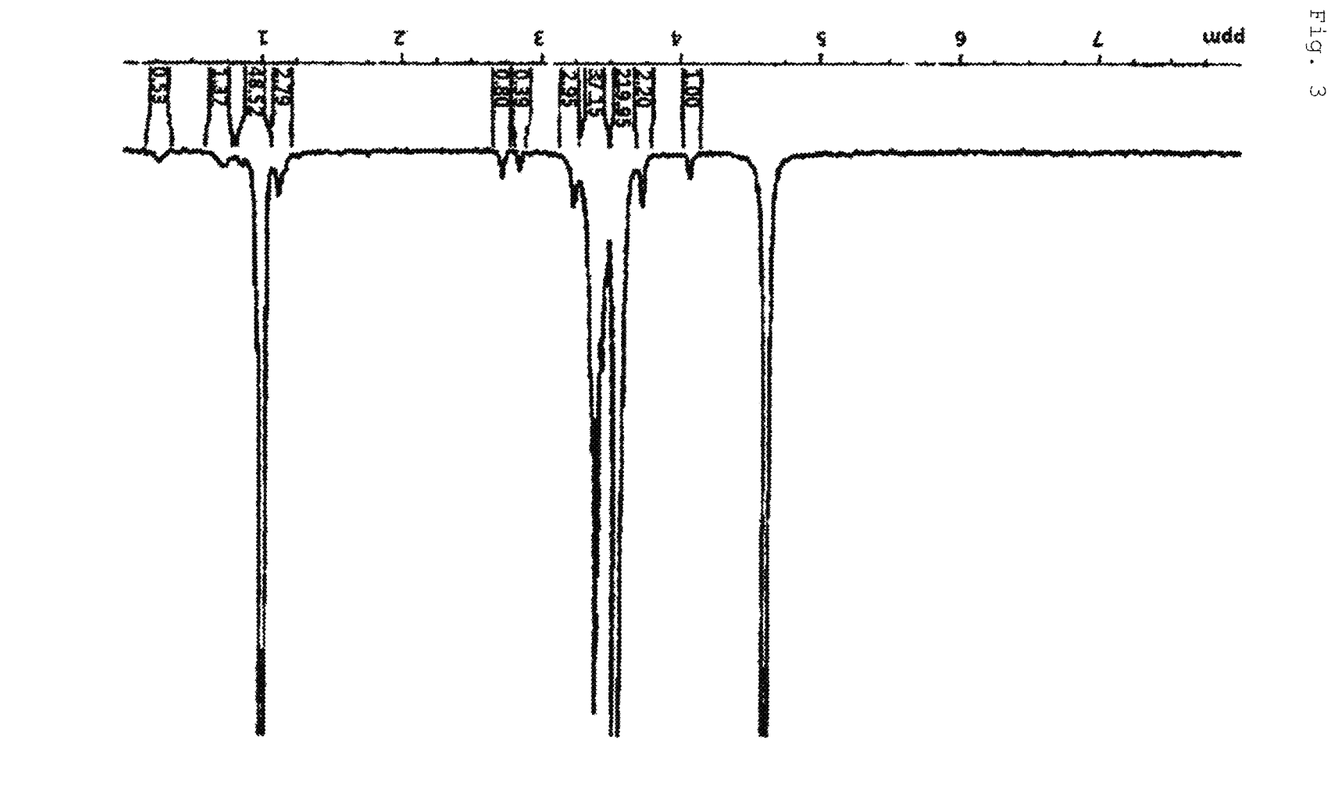
FIG. 3 is the nuclear magnetic resonance spectrum of a Pluronic having a thiol group-coupled to both ends thereof, prepared in Preparation Example 2.

FIG. 3 shows a graph obtained by analyzing the thiol group-coupled Pluronic by nuclear magnetic resonance spectrometry. It was shown that the content of the thiol group per Pluronic molecule was 78%.

Example 1

Preparation of Hydrogel Comprising Catechol Group-Coupled Chitosan and Pluronic Having Thiol Group Coupled to End Thereof 0.1 g of the catechol group-coupled chitosan prepared in Preparation Example 1 was dissolved in 10 g of phosphate buffered saline (PBS, pH 7.4) to make a chitosan solution, and 2.4 g of the Pluronic having the thiol group coupled to the end thereof, prepared in Preparation Example 2, was dissolved in 10 g of phosphate buffered saline (PBS, pH 7.4) to make a Pluronic solution. 5 g of the chitosan solution and 5 g of the Pluronic solution were mixed to each other to prepare a hydrogel solution.

Gelation of the hydrogel solution was investigated using the vial tilting method known in the art at temperatures between 0° C. and 90° C. with intervals of 1° C. As a result, it was visually observed that a non-flowable hydrogel was prepared when the hydrogel solution was maintained at a temperature between 4° C. and 37° C. for 5 minutes.

Example 2

Preparation of Hydrogel Comprising Catechol Group-Coupled Chitosan and Pluronic Having Thiol Group Coupled to End Thereof The procedure of Example 1 was repeated, except that 0.1 g of the catechol group-coupled chitosan prepared in Preparation Example 1 was dissolved in 10 g of phosphate buffered saline (PBS, pH 7.4) to make a chitosan solution and that 3.2 g of the Pluronic having the thiol group coupled to the end thereof, prepared in Preparation Example 2, was dissolved in 10 g of phosphate buffered saline (PBS, pH 7.4) to make a Pluronic solution.

Example 3

Preparation of Hydrogel Comprising Catechol Group-Coupled Chitosan and Pluronic Having Thiol Group Coupled to End Thereof The procedure of Example 1 was repeated, except that 0.2 g of the catechol group-coupled chitosan prepared in Preparation Example 1 was dissolved in 10 g of phosphate buffered saline (PBS, pH 7.4) to make a chitosan solution and that 2.4 g of the Pluronic having the thiol group coupled to the end thereof, prepared in Preparation Example 2, was dissolved in 10 g of phosphate buffered saline (PBS, pH 7.4) to make a Pluronic solution.

Example 4

Preparation of Hydrogel Comprising Catechol Group-Coupled Chitosan and Pluronic Having Thiol Group Coupled to End Thereof The procedure of Example 1 was repeated, except that 0.2 g of the catechol group-coupled chitosan prepared in Preparation Example 1 was dissolved in 10 g of phosphate buffered saline (PBS, pH 7.4) to make a chitosan solution and that 3.6 g of the Pluronic having the thiol group coupled to the end thereof, prepared in Preparation Example 2, was dissolved in 10 g of phosphate buffered saline (PBS, pH 7.4) to make a Pluronic solution.

Comparative Example 1

Preparation of Hydrogel Comprising Chitosan

The procedure of Example 1 was repeated, except that chitosan (chitosan 300) was used instead of the catechol group-coupled chitosan prepared in Preparation Example 1 and the Pluronic having the thiol group coupled to the end thereof, prepared in Preparation Example 2.

Comparative Example 2

Preparation of Hydrogel Comprising Catechol Group-Coupled Chitosan

The procedure of Example 1 was repeated, except that the Pluronic having the thiol group coupled to the end thereof, prepared in Preparation Example 2, was not used.

Comparative Example 3

Preparation of Hydrogel Comprising Pluronic

The procedure of Example 1 was repeated, except that Pluronic (Pluronic F-127) was used instead of the catechol group-coupled chitosan prepared in Preparation Example 1 and the Pluronic having the thiol group coupled to the end thereof, prepared in Preparation Example 2.

Comparative Example 4

Preparation of Hydrogel Comprising Pluronic Having Thiol Group Coupled to End Thereof The procedure of Example 1 was repeated, except that the catechol group-coupled chitosan prepared in Preparation Example 1 was not used.

Comparative Example 5

Preparation of Hydrogel Comprising Chitosan and Pluronic

The procedure of Example 1 was repeated, except that chitosan (chitosan 300) was used instead of the catechol group-coupled chitosan prepared in Preparation Example 1 and that Pluronic (Pluronic F-127) was used instead of the Pluronic having the thiol group coupled to the end thereof, prepared in Preparation Example 2.

Comparative Example 6

Preparation of Hydrogel Comprising Chitosan and Pluronic Having Thiol Group Coupled to End Thereof The procedure of Example 1 was repeated, except that chitosan (chitosan 300) was used instead of instead of the catechol group-coupled chitosan prepared in Preparation Example 1

Comparative Example 7

Preparation of Hydrogel Comprising Catechol Group-Coupled Chitosan and Pluronic

The procedure of Example 1 was repeated, except that Pluronic (Pluronic F-127) was used instead of the Pluronic having the thiol group coupled to the end thereof, prepared in Preparation Example 2.

Test Example 1

Measurement of In Vitro Erosion of Hydrogel

In order to measure the erosion of hydrogel with time, 1 ml of the hydrogel prepared in Example 1 was placed in a 2-ml tube, and 1 ml of PBS (pH 7.4) was added thereto, after which the mass of the remaining mass of the hydrogel was compared with the initial mass of the hydrogel to determine the erosion of the hydrogel. The erosion of the hydrogel means the stability of the hydrogel. Quick erosion of the hydrogel can be advantageous for short-term treatment, and slow erosion of the hydrogel can be advantageous for long-term treatment. The hydrogel prepared in Example 1 showed residual rates of 100 mass % after 12 hours, 100 mass % after 1 day, 94.43 mass % after 2 days, 80.09 mass % after 7 days, 72.02 mass % after 14 days, and 66.83% mass % after 31 days.

Test Example 2

Measurement of In Vitro Erosion of Hydrogel

The procedure of Test Example 1 was repeated, except that the hydrogel prepared in Example 2 was used. As a result, it was shown that the hydrogel showed residual rates of 100 mass % after 12 hours, 100 mass % after 1 day, 100 mass % after 2 days, 100 mass % after 7 days, 100 mass % after 14 days, and 100 mass % after 31 days.

Test Example 3

Measurement of In Vitro Erosion of Hydrogel

The procedure of Test Example 1 was repeated, except that the hydrogel prepared in Example 3 was used. As a result, it was shown that the hydrogel showed residual rates of 100 mass % after 12 hours, 100 mass % after 1 day, 100 mass % after 2 days, 95.91 mass % after 7 days, 64.76 mass % after 14 days, and 23.70 mass % after 31 days.

Test Example 4

Measurement of In Vitro Erosion of Hydrogel

The procedure of Test Example 1 was repeated, except that the hydrogel prepared in Example 4 was used. As a result, it was shown that the hydrogel showed residual rates of 100 mass % after 12 hours, 100 mass % after 1 day, 100 mass % after 2 days, 100 mass % after 7 days, 80.26 mass % after 14 days, and 42.33 mass % after 31 days.

The results of Test Examples 1 to 4 indicated that the erosion of the hydrogel according to the present invention can be controlled by changing the ratio between the catechol group-coupled chitosan and the Pluronic having the thiol group coupled to the end thereof.

Comparative Test Example 1

Measurement of In Vitro Erosion of Hydrogel

The procedure of Test Example 1 was repeated, except that the hydrogel prepared in Comparative Example 3 was used. As a result, it was shown that the hydrogel showed residual rates of 60 mass % after 12 hours, 17 mass % after 1 day, 4 mass % after 2 days, 0 mass % after 7 days, 0 mass % after 14 days, and 0 mass % after 31 days.

Test Example 5

Measurement of In Vivo Erosion of Hydrogel

In order to measure the erosion of the hydrogel in vivo, a rat model (BALB/c, 21-23 g, 8w, M) was used. 500 µl of the hydrogel prepared in Example 1 was injected subcutaneously into a rat, and then the erosion of the hydrogel was measured with time by comparing the remaining mass of the hydrogel with the initial mass of the hydrogel. The in vivo stability of the hydrogel was measured based on the result of in vitro erosion, and as a result, it was shown that the hydrogel prepared in Example 1 showed residual rates of 100 mass % after 1 day, 100 mass % after 7 days, 81.28 mass % after 14 days, and 75.04 mass % after 25 days.

Test Example 6

Measurement of In Vivo Erosion of Hydrogel

The procedure of Test Example 5 was repeated, except that the hydrogel prepared in Example 2 was used. As a result, it was shown that the hydrogel showed residual rates of 100 mass % after 1 day, 100 mass % after 7 days, 98.67 mass % after 14 days, and 97.45 mass % after 25 days.

The results of Test Examples 5 and 6 indicated that the erosion of the hydrogel according to the present invention can be controlled by changing the ratio between the catechol group-coupled chitosan and the Pluronic having the thiol group coupled to the end thereof and that the hydrogel according to the present invention has excellent stability in vivo.

Comparative Test Example 2

Measurement of In Vivo Erosion of Hydrogel

The procedure of Test Example 5 was repeated, except that the hydrogel prepared in Comparative Example 3 was used. As a result, it was shown that the hydrogel showed residual rates of 30 mass % after 1 day, 0 mass % after 7 days, 0 mass % after 14 days, and 0 mass % after 25 days.

Test Example 7

Analysis of Tissue Adhesion Property

Figure 4:
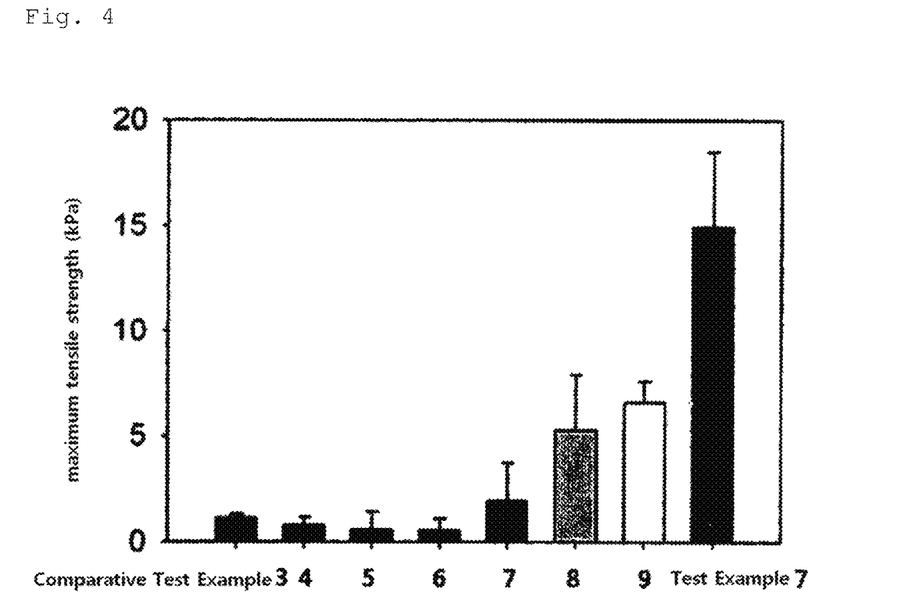
FIG. 4 is a graphic diagram showing the results of measuring the adhesive strengths of hydrogels in Comparative Test Examples 3 to 9 and Test Example 7.

To analyze the tissue adhesion property of the hydrogel, a universal testing machine (UTM) equipped with a 150N load cell together with a hydrogel holder was used. First, the rat's subcutaneous tissue was obtained by needle biopsy using a 6-mm punch and attached to a cylindrical detector using a commercially available instant adhesive (cyanoacrylate glue). 0.1 g of the hydrogel prepared in Example 1 was located in the holder on the universal testing machine, and the cylindrical detector having the subcutaneous tissue attached thereto was pressed with a force of 0.1 mN for 5 minutes. The temperature of the holder portion was set at 37° C., and the tensile strength was measured while pulling the holder. The results of the measurement are shown in FIG. 4.

Comparative Test Example 3

Analysis of Tissue Adhesion Property

The procedure of Test Example 7 was repeated, except that the hydrogel prepared in Comparative Example 1 was used. The results of the measurement are shown in FIG. 4.

Comparative Test Example 4

Analysis of Tissue Adhesion Property

The procedure of Test Example 7 was repeated, except that the hydrogel prepared in Comparative Example 2 was used. The results of the measurement are shown in FIG. 4.

Comparative Test Example 5

Analysis of Tissue Adhesion Property

The procedure of Test Example 7 was repeated, except that the hydrogel prepared in Comparative Example 3 was used. The results of the measurement are shown in FIG. 4.

Comparative Test Example 6

Analysis of Tissue Adhesion Property

The procedure of Test Example 7 was repeated, except that the hydrogel prepared in Comparative Example 4 was used. The results of the measurement are shown in FIG. 4.

Comparative Test Example 7

Analysis of Tissue Adhesion Property

The procedure of Test Example 7 was repeated, except that the hydrogel prepared in Comparative Example 5 was used. The results of the measurement are shown in FIG. 4.

Comparative Test Example 8

Analysis of Tissue Adhesion Property

The procedure of Test Example 7 was repeated, except that the hydrogel prepared in Comparative Example 6 was used. The results of the measurement are shown in FIG. 4.

Comparative Test Example 9

Analysis of Tissue Adhesion Property

The procedure of Test Example 7 was repeated, except that the hydrogel prepared in Comparative Example 7 was used. The results of the measurement are shown in FIG. 4.

Test Example 8

Analysis of Hemostatic Effect

Figure 5:
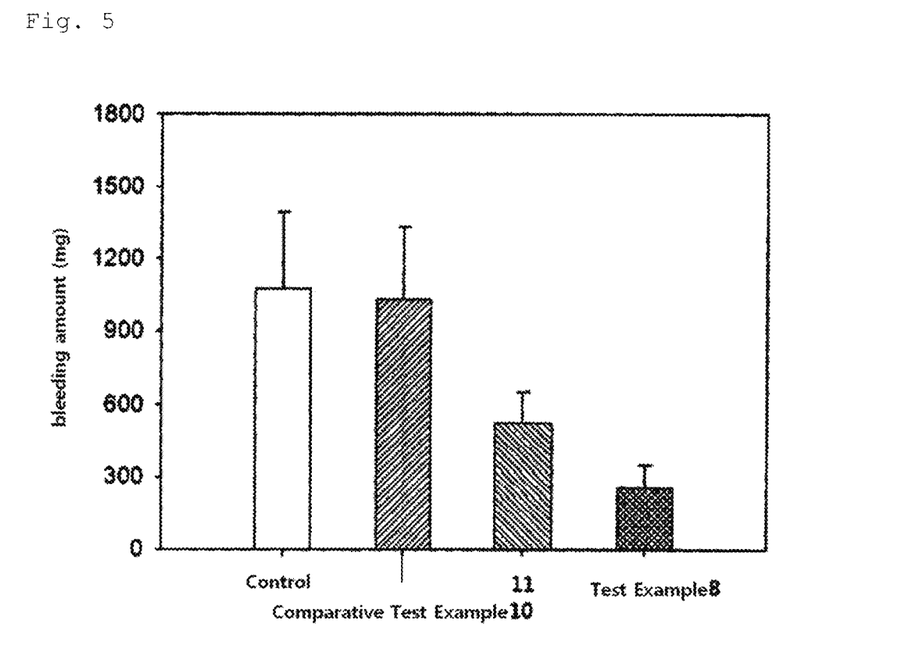
FIG. 5 is a graphic diagram showing the results of measuring the hemostatic effects of hydrogels in Comparative Test Examples 10 and 11, a control group and Test Example 8.

To analyze the hemostatic effect of the hydrogel in vivo, the abdominal cavity of rats (normal SD rat, 185-200 g, 5w, M) was incised to construct bleeding liver models. First, rats were anesthetized with ketamine on an operating table, and then the abdomen was incised. Then, weighed filter paper was placed on a para-film and located under the liver. In a control group, the liver was injured by a 18 G syringe needle, and the amount of bleeding was measured, and in a test group, the hydrogel prepared in Example 1 was injected immediately after the liver was injured by 18 G syringe needle, and the amount of bleeding was measured. The results of the measurement are shown in FIG. 5.

Comparative Test Example 10

Analysis of Hemostatic Effect

The procedure of Test Example 8 was repeated, except that the hydrogel prepared in Comparative Example 2 was used. The results of the measurement are shown in FIG. 5.

Comparative Test Example 11

Analysis of Hemostatic Effect

The procedure of Test Example 8 was repeated, except that the hydrogel prepared in Comparative Example 4 was used. The results of the measurement are shown in FIG. 5.

The invention claimed is:
1. A temperature sensitive hydrogel composition comprising: (i) a chitosan, covalently bound to catechol groups along its backbone; and (ii) a poloxamer containing terminal thiol groups, wherein each sulfur from said terminal thiol groups of the poloxamer is bound to a different catechol group, as respective sulfur-bound catechol groups, and wherein each of the sulfur-bound catechol group contains dihydroxy functional groups.
2. The hydrogel composition of claim 1, wherein said chitosan, covalently bound to catechol groups along its backbone, has a molecular weight of 10,000 Da-1,000,000 Da.
3. The hydrogel composition of claim 1, wherein said chitosan, covalently bound to catechol groups along its backbone, has a molecular weight of 50,000 Da-200,000 Da.

4. The hydrogel composition of claim 1,
wherein said poloxamer comprises a block copolymer represented by the following formula 2, to which thiol groups have been coupled to the termini:

Formula 2 wherein a is an integer in a range of from 2 to 200; b is an integer in a range of from 10 to 100; and the ratio of a:b is in a range of from 1:9 to 8:2;
or a block copolymer represented by the following Formula 3, to which thiol groups have been coupled to the termini:

Formula 3 wherein a is an integer in a range of from 2 to 600; b is an integer in a range of from 10 to 150; and the ratio of a:b is in a range of from 1:9 to 9:1.

5. The hydrogel composition of claim 1, wherein the hydrogel composition further comprises a therapeutic drug.

6. The hydrogel composition of claim 5, wherein the therapeutic drug is one or more selected from the group consisting of human growth hormones, erythropoietin, interferon, insulin, interleukin, calcitonin, G-CSF, Angiopoietin, VEGF-Trap, monoclonal antibodies, antibody fragments, hemostatic proteins, antibiotics, analgesics, angina therapeutic agents, allergen extract, anti-histamines, and anti-allergic agents.

7. A hemostat comprising the hydrogel composition of claim 1.

8. A method for preparing a hydrogel, the method comprising:
(A) preparing a chitosan, covalently bound to catechol groups along its backbone;
(B) preparing a poloxamer containing terminal thiol groups;
(C) preparing a catechol-chitosan solution by dissolving the chitosan, covalently bound to catechol groups along its backbone, in a buffer;
(D) preparing a thiol-poloxamer solution by dissolving the poloxamer containing terminal thiol groups in a buffer;
(E) preparing an adhesive hydrogel solution by mixing the catechol-chitosan solution of step (C) with the thiol-poloxamer solution of step (D); and
(F) gelating the adhesive hydrogel solution of step (E).

9. The method of claim 8, wherein step (A) of preparing the chitosan, covalently bound to catechol groups along its backbone, comprises the steps of:
(a) preparing a chitosan solution by adding 0.2-5 parts by weight of chitosan to 100 parts by weight of distilled water;
(b) preparing a hydrocaffeic acid solution by adding 1-5 parts by weight of hydrocaffeic acid and 2-10 parts by weight of 1-ethyl-3-(3-dimethylaminopropyl)-carbodiimide hydrochloride (EDC) to 100 parts by weight of distilled water;
(c) preparing a mixture of chitosan, covalently bound to catechol groups along its backbone, by mixing the chitosan solution of step (a) with the hydrocaffeic acid solution of step (b) at a volume ratio of 1:1 to 3:1 and stirring the mixture; and
(d) purifying the chitosan, covalently bound to catechol groups along its backbone, by dialyzing the mixture of chitosan, covalently bound to catechol groups along its backbone, of step (c) through a dialysis membrane in a buffer for 6-48 hours, and then drying purified chitosan, covalently bound to catechol groups along its backbone.

10. The method of claim 8, wherein step (B) of preparing the poloxamer containing terminal thiol groups comprising the steps of:
(1) preparing a poloxamer solution by adding 5-15 parts by weight of poloxamer to 100 parts by weight of a non-polar organic solvent and 0.1-1 part by volume of triethylamine to 100 parts by volume of the non-polar organic solvent;
(2) preparing a nitrophenyl chloroformate solution by adding 5-20 parts by weight of nitrophenyl chloroformate to 100 parts by weight of a non-polar organic solvent;
(3) preparing a poloxamer mixture solution by mixing the poloxamer solution of step (1) with the nitrophenyl chloroformate solution of step (2) at a volume ratio of 5:1 to 10:1, and stirring the mixture;
(4) preparing a poloxamer mixture by precipitating and drying the poloxamer mixture solution of step (3);
(5) preparing a mixture of poloxamer containing terminal thiol groups by adding 5-20 parts by weight of the poloxamer mixture of step (4) and 0.2-5 parts by weight of cysteamine to 100 parts by weight of a mixture of a non-polar organic solvent and a polar solvent, and stirring the mixture;
(6) preparing a block copolymer mixture containing terminal thiol groups by precipitating and drying the mixture of poloxamer containing a thiol group of step (5); and
(7) purifying the block copolymer containing terminal thiol groups by dialyzing the block copolymer mixture containing terminal thiol groups of step (6) through a dialysis membrane in distilled water for 12-120 hours, and then drying to produce a purified block copolymer containing terminal thiol groups.

11. The method of claim 8, wherein the catechol-chitosan solution of step (C) is prepared by adding 0.1-10 wt % of the chitosan, covalently bound to catechol groups along its backbone, to the buffer.

12. The method of claim 8, wherein the thiol-poloxamer solution of step (D) is prepared by adding 3-50 wt % of the poloxamer containing terminal thiol groups, to 100 wt % of the buffer.

13. The method of claim 8, wherein the adhesive hydrogel solution of step (E) is prepared by mixing the catechol-chitosan solution with the thiol-poloxamer solution at a volume ratio of 1:3 to 3:1.

14. The method of claim 8, wherein step (F) is carried out at a temperature of 4 to 37° C.

15. The method of claim 9, wherein each of the catechol groups in step (A) is represented by the following formula 1:

Formula 1 wherein the chitosan, covalently bound to the catechol groups along its backbone, has a molecular weight of 10 kDa-1,000 kDa.

16. The method of claim 10, wherein the poloxamer containing terminal thiol groups of step (B) comprises a block copolymer represented by the following formula 2, to which terminal thiol groups have been coupled at the termini:

Formula 2 wherein a is an integer in a range of from 2 to 200; b is an integer in a range of from 10 to 100; and the ratio of a:b is in a range of from 1:9 to 8:2; and or a block copolymer represented by the following Formula 3, to which terminal thiol groups have been coupled to the termini:

Formula 3 wherein a is an integer in a range of from 2 to 600; b is an integer in a range of from 10 to 150; and the ratio of a:b is in a range of from 1:9 to 9:1.

* * * * *

UNITED STATES PATENT AND TRADEMARK OFFICE
CERTIFICATE OF CORRECTION

PATENT NO. : 9,433,699 B2
APPLICATION NO. : 14/239538
DATED : September 6, 2016
INVENTOR(S) : Haeshin Lee et al.

It is certified that error appears in the above-identified patent and that said Letters Patent is hereby corrected as shown below:

IN THE SPECIFICATION

Column 7, line 5: "0.1-wt % of" should be --0.1-20 wt % of--.

Signed and Sealed this
Twenty-fifth Day of October, 2016

Michelle K. Lee
*Director of the United States Patent and Trademark Office*